United States Patent
Veenstra et al.

(10) Patent No.: US 9,610,282 B2
(45) Date of Patent: Apr. 4, 2017

(54) COMPOSITIONS AND METHODS FOR PREVENTING INFECTION OF A WOUND AND FOR ADVANCING THE HEALING PROCESS

(71) Applicant: NBIP, LLC, Plano, TX (US)

(72) Inventors: John W. Veenstra, Richardson, TX (US); Burt R. Sookram, Palm Harbor, FL (US)

(73) Assignee: NBIP, LLC, Richardson, TX (US)

(*) Notice: Subject to any disclaimer, the term of this patent is extended or adjusted under 35 U.S.C. 154(b) by 0 days.

(21) Appl. No.: 14/775,713

(22) PCT Filed: Mar. 12, 2014

(86) PCT No.: PCT/US2014/024989
§ 371 (c)(1),
(2) Date: Sep. 13, 2015

(87) PCT Pub. No.: WO2014/165253
PCT Pub. Date: Oct. 9, 2014

(65) Prior Publication Data
US 2016/0022655 A1    Jan. 28, 2016

Related U.S. Application Data

(60) Provisional application No. 61/778,205, filed on Mar. 12, 2013.

(51) Int. Cl.
| | | |
|---|---|---|
| *A61K 31/4425* | (2006.01) | |
| *A01N 43/40* | (2006.01) | |
| *A61K 31/14* | (2006.01) | |
| *A61K 31/194* | (2006.01) | |
| *A61K 31/60* | (2006.01) | |
| *A61K 33/00* | (2006.01) | |
| *A61K 33/38* | (2006.01) | |
| *A61K 33/40* | (2006.01) | |
| *A61K 31/19* | (2006.01) | |
| *A61K 31/198* | (2006.01) | |
| *A61K 47/38* | (2006.01) | |
| *A61K 31/714* | (2006.01) | |
| *A61K 33/14* | (2006.01) | |
| *A61K 31/7004* | (2006.01) | |
| *A61K 31/455* | (2006.01) | |
| *A61K 31/4188* | (2006.01) | |
| *A61K 31/675* | (2006.01) | |
| *A61K 38/43* | (2006.01) | |
| *A61K 33/04* | (2006.01) | |
| *A61K 33/30* | (2006.01) | |
| *A61K 36/61* | (2006.01) | |
| *A61K 9/00* | (2006.01) | |
| *A61K 33/06* | (2006.01) | |

(52) U.S. Cl.
CPC .......... *A61K 31/4425* (2013.01); *A01N 43/40* (2013.01); *A61K 9/0014* (2013.01); *A61K 31/14* (2013.01); *A61K 31/19* (2013.01); *A61K 31/194* (2013.01); *A61K 31/198* (2013.01); *A61K 31/4188* (2013.01); *A61K 31/455* (2013.01); *A61K 31/60* (2013.01); *A61K 31/675* (2013.01); *A61K 31/7004* (2013.01); *A61K 31/714* (2013.01); *A61K 33/00* (2013.01); *A61K 33/04* (2013.01); *A61K 33/06* (2013.01); *A61K 33/14* (2013.01); *A61K 33/30* (2013.01); *A61K 33/38* (2013.01); *A61K 33/40* (2013.01); *A61K 36/61* (2013.01); *A61K 38/43* (2013.01); *A61K 47/38* (2013.01)

(58) Field of Classification Search
CPC .............. A61K 31/675; A61K 31/7004; A61K 31/714; A61K 31/14; A61K 31/194; A61K 31/60; A61K 31/4425; A61K 31/4188; A61K 31/198; A61K 31/19; A61K 31/455; A61K 33/00; A61K 33/04; A61K 33/30; A61K 33/38; A61K 33/40; A61K 33/14; A61K 47/38; A61K 38/43; A61K 36/61; A01N 43/40; A01N 25/02
See application file for complete search history.

(56) References Cited

U.S. PATENT DOCUMENTS

| | | | | |
|---|---|---|---|---|
| 2005/0232974 A1* | 10/2005 | Gore | .................... | A61K 9/1075 424/439 |
| 2007/0299043 A1* | 12/2007 | Hunter | .................. | A61F 2/0077 514/171 |
| 2009/0123429 A1 | 5/2009 | Duncan et al. | | |
| 2010/0331350 A1* | 12/2010 | Honigberg | .............. | A61K 31/00 514/265.1 |
| 2011/0118243 A1* | 5/2011 | Chambers | ............ | A61K 9/0056 514/226.5 |
| 2012/0177747 A1* | 7/2012 | Sookram | ................ | A01N 43/40 424/637 |

OTHER PUBLICATIONS

What is Bacterial Vaginosis? at http://www.everydayhealth.com/bacterial-vaginosis/guide/ --- Diana Rodriquez Apr. 21, 2016.*

* cited by examiner

*Primary Examiner* — Blessing M Fubara
(74) *Attorney, Agent, or Firm* — Winstead PC

(57) ABSTRACT

The present disclosure relates to compositions and methods that are effective in controlling and preventing bacterial, viral and fungal infections in the living tissue of plants, humans and animals, and in advancing the healing process for wounds to that tissue. The disclosed compositions comprise a biocidal system, a pH buffer, and one or more of a surfactant, a cellular energy supplement, an inflammation reducer, a clotting agent, an electrolytic system, a lattice forming system, and for plants a fungicide, all in an aqueous composition.

18 Claims, No Drawings

COMPOSITIONS AND METHODS FOR PREVENTING INFECTION OF A WOUND AND FOR ADVANCING THE HEALING PROCESS

CROSS-REFERENCES TO RELATED APPLICATIONS

This Application claims the benefit under 35 U.S.C. §119(e) of U.S. Provisional Patent Application No. 61/778,205 filed Mar. 12, 2013 which is incorporated herein by reference in its entirety as if fully set forth herein.

FIELD OF THE INVENTION

The present disclosure relates to compositions and methods that are effective in controlling and preventing bacterial, viral and fungal infections in the living tissue of plants, humans and animals, and in advancing the healing process for wounds to that tissue.

BACKGROUND OF THE INVENTION

In human and animal medicine, a wound is a type of injury in which living tissue or skin is torn, cut or punctured (an open wound), or where blunt force trauma causes a contusion (a closed wound). In pathology, it specifically refers to a sharp injury which damages the dermis of the skin.

A wound is also defined as an injury that causes either an internal or external break in body tissue. An open wound is a break in the skin or mucous membrane. Open wounds occur when the upper skin layer has been damaged. The damage may show as a cut, puncture or tear and most wounds are susceptible to infection from bacteria, viruses and fungi. Some open wound infections may require emergency medical treatment. Wounds may or may not involve a break in the skids upper layer. Wounds without breakage are classified as closed, while open wounds show breakage. Open wounds such as abrasions and lacerations may not require direct medical care, while punctures are more likely to be infected and require care. Some wounds may be large enough to require stitches from a doctor to close and seal the wound prior to healing.

There are at least five different types of open wounds:

An abrasion is a skin wound caused by rubbing or scraping the skin against a hard, rough surface. Bleeding in this type of wound is usually limited, but it is important that the skin be cleaned in order to guard against infection.

An incision is a cut caused by a knife, the rough edge of metal, broken glass, a razor blade or some other sharp object. This type of wound generally bleeds rapidly and heavily. If the cut is deep, muscles, tendons and nerves may be damaged and require stitches.

A laceration is a jagged, irregular or blunt breaking or tearing of soft tissues, often resulting from mishandling tools and machinery and other accidents. Bleeding from a laceration may be rapid and extensive. Again, stitches may be required.

A puncture is a piercing wound that causes a small hole in the tissues. Such objects as nails, needles, ice picks and other pointed objects can produce puncture wounds. Even if external bleeding is slight, there may be serious internal bleeding resulting from internal damage to an organ such as in a gunshot wound. All puncture wounds require the attention of a health professional because of the danger of tetanus.

An avulsion is a forcible tearing or partial tearing away of tissues. It occurs in such accidents as gunshot wounds, explosions, animal bites or other body-crushing injuries. Bleeding is heavy and rapid.

Causes of Infection

When a large number of bacteria, viruses or fungi get into a wound, the wound can get infected. The most common type of infection comes from bacteria but more than one type of bacteria may infect a wound at the same time. Common bacteria that live on the skin often enter a wound first. A break in the skin gives them a chance to enter and cause infection. Bacteria may also come from the environment, such as soil, air, or water. If an object such as a nail caused the wound, bacteria may come from that source. If you are bitten by an animal, bug, insect or person, their saliva can also cause infection. Mosquitos can also infect living tissues from the bacteria and viruses they transmit via a bite.

Infection Types

One type of infection is cellulitis which is an inflammation of the skin caused by bacteria. Necrotizing subcutaneous infection is a severe infection caused by bacteria that infect the tissue through wounds. The primary symptoms are swelling, discoloration and death of the surrounding tissue. The skin around the wound becomes hot, inflamed, tender and red. If the infection worsens, the skin may become discolored and gangrene may develop. Gangrene, can result in death or decay of tissues which means the infected part needs to be removed.

"Gas gangrene" results when a wound becomes infected by certain bacteria, usually *Clostridium*. This infection causes sudden pain and swelling around the wound, moderate increase in temperature, decrease in blood pressure and rapid heartbeat. Skin around the wound becomes pale, due to fluid that builds under it and a watery, foul-smelling; brownish-red fluid may be released. The tissue color changes from pale to dusky color as the infection worsens. Most common treatment consists of penicillin given intravenously but, if that fails, the infected tissue is surgically removed.

Anyone who has a wound can develop an infection. However some people are more susceptible. People with poor healing abilities like the elderly are more susceptible because of their declining immune system. Also people who do not eat the right foods and lack vitamins, nutrients or have protein deficiency are also at higher risk. The chronically ill, bedridden or non-ambulatory are also at risk as well as people who have undergone prolonged corticosteroid use or have been administered a potent immunosuppressive drug. Radiation therapy patients, diabetics, the obese and those that have had a stroke or some sort of vascular disease are also more likely to develop some sort of wound infection.

Infection Causes

Microbiological contamination has long been a major concern for the health of living tissue because of the spread of fungi, bacteria and viruses. There has been increasing awareness of the problem in recent years due to outbreaks of *E. coli*, cryptosporidiosis, and hepatitis. Certain medical conditions, such as diabetes and AIDS can also leave a wound victim at higher risk. While many infections are caused by bacteria, others are caused by viruses, parasites and Fungi.

Bacteria

Bacteria are tiny organisms. Not all types of bacteria are harmful to living tissues. Bacteria can be separated into two groups:
1) pathogenic (disease causing) and
2) non-pathogenic (not disease causing).

Bacteria such as some *Staphylococcus* species, *Corynebacterium* spp., *Brevibacterium* spp and *Acinetobacter* live on healthy skin and cause no harm. *Propionibacteria* live in the hair follicles of adult skin and contribute to acne.

Some bacteria invade through broken skin from eczema or wounds inflicted by insect bites. Bacterial infection may result in symptoms ranging from rashes to gangrene. The most common bacteria that cause skin infections are:

*Staphylococcus aureus* causes furunculosis (boils) impetigo (sores), toxic shock syndrome, tropical pyomyositis and botryomycosis.

*Streptococcus pyogenes* causes cellulitis, scarlet fever, rheumatic fever, erysipelas.

*Haemophilus* specie causes chancroid and cellulitis.

*Pseudomonas aeruginosa* causes wound infections and athlete's foot.

*Clostridium perfringens* and other species which causes gas gangrene.

*Bartonella* species causes catscratch fever and bartonellosis.

*Fusibacterium* species, *Bacillus fusiformis*, *Treponema vincenti* and other bacteria which may result in tropical ulcers.

Viruses

The smallest of the infectious microorganisms is that group of viruses, some of which are parasitic. Too small to be seen without the use of a microscope, viruses are capable of causing disease in humans, plants and animals. Viruses can pass through porcelain filters that are capable of screening out bacteria. Infectious viruses such as hepatitis, poliomyelitis, meningitis, and gastroenteritis, rotaviruses, norwalk virus and other caliciviruses are all microbes which can be found on contaminated surface and in the air. A virus is a minute (0.004 to 0.1 micron) infectious agent that is incapable of growth except in the presence of a host environment.

Common viruses found in our everyday life are:
a) *Cryptosporidium*, a single-celled microbe contained in a group generally known as parasites which cause disease, when ingested. Symptoms occur 2 to 10 days after infection and include diarrhea, headache, abdominal cramps, nausea, vomiting, and a low fever.
b) Oocysts are a stage in the life-cycle of some *Cryptosporidium*. In this stage, the *Cryptosporidium* can infect humans and other animals.
c) *Giardia lamblia* commonly referred to as *Giardia*, are single-celled microbes contained in a group known as parasites. When infected, they cause a gastrointestinal disease with frequent diarrhea, fatigue and cramps.
d) Hepatitis is an enteric virus that is transferred through blood contamination. The symptoms range from an inflamed liver, anorexia, weakness, nausea, fever and jaundice. Infection may last a week or two, but a severe case can result in liver damage and even death.

Fungi

Plant fungus is classified into the following four categories:

1. Vascular wilt, foliar/shoot, root and butt rot, and canker. Vascular type fungus blocks nutrients from reaching the tree. Symptoms include early leaf drop and wilting.
2. Foliar/shoot type fungus is the most common type of tree fungus. It affects the leaves, leaving spots, and causing mostly aesthetic damage.
3. Root and butt rot kill the roots and trunk of a tree. This type of fungus is mostly a-symptomatic, until the tree is beyond saving.
4. Canker type fungus infections typically occur when a branch is pruned and the stub is left untreated. It leaves a sunken appearance to the surrounding bark.
5. Bracket fungi, or shelf fungi, among many groups of the fungi in the phylum basidiomycota. These are shelf- or bracket-shaped fruiting bodies called conks that lie in a close planar grouping of separate or interconnected horizontal rows. Brackets can single row of a few caps, to dozens of rows of caps and are typically tough and sturdy and produce their spores. They are mainly found on all types of trees both living and dead, coarse woody debris, and may resemble mushrooms. Bracket fungi are defined by their growth form rather than phylogeny, the group contains members of multiple clades and is called polypores. The beefsteak fungus is actually a member of the agarics. Other examples of bracket fungi include the sulphur shelf, birch bracket, dryad's saddle, artist's conk, and turkey tail.
6. The conidia germinate to form appressoria on plant surfaces. Infection may occur through almost any plant surface, but for herbaceous species such as strawberry and anemone, the crown with its relatively humid microclimate is often favored. In suitable conditions, the fungus can grow rapidly inside the plant and cause severe symptoms very quickly, but in other circumstances the fungus may be quiescent inside host tissues for a period, in some cases only becoming apparent after harvest. Once the fungus has developed sufficiently inside the plant, dark fruit-bodies are produced, causing typical anthracnose symptoms. Conidia are formed liberally, and are normally dispersed by irrigation. They may lie dormant in the soil for some time, often overwintering, and able to survive longer under relatively cool, dry conditions. The fungus can also remain dangerous for long periods in dead plant material on the surface or buried in the soil.

The species has a very wide host range, but is economically most important on strawberries. Other cultivated hosts include *Anemone coronaria*, apples, aubergines, avocados, celery, coffee, guavas, olives, papayas, tomatillos, tomatoes and citrus.

Standard Treatments

Physical treatment of a human or animal wound depends on the type, cause, and depth of the wound as well as whether the structure below the skin is damaged. Treatment of recent lacerations involves examination, cleaning, and closing the wound. Minor wounds, like bruises, usually heal on their own with some skin discoloration. Abrasions, which are wounds with intact skin, usually require no active treatment except keeping the area clean. Puncture wounds may be prone to infection depending on the depth of penetration. The entry point of a puncture wound is often left open to allow for bacteria or debris to be removed. Wounds caused by a knife or a sharp object need to be thoroughly cleaned and the edges trimmed. If the wounds are fresh and less than 12 hours old, they can be closed using bandages, a cyanoacrylate glue, staples or sutures.

In order to prevent or treat microbiological contamination of a wound, the health-care industry generally uses one or more of the following topical or internal applications to address infections:

1) Antibiotics such as penicillin, tetracycline, oxytetracycline and lincomycin. Antibiotics are chemical substances produced by a micro-organism that have the capacity, in dilute solutions, to selectively inhibit the growth of or to kill other micro-organisms. Whereas it is now generally accepted that systemic antibiotics are essential for the management of clinically infected wounds, the choice of antibiotic to be used is not always apparent.

2) Silver, which interferes with the bacterial electron transport system and inhibits the multiplication of the bacteria. However, to achieve this, silver ions have to be able to enter a cell. The chemical bonding of silver with a sulphonamide antimicrobial—sulphadiazine—has resulted in the development of a safe broad-spectrum agent for topical use. In this formulation silver is released slowly from the transport medium in concentrations that are selectively toxic to micro-organisms such as bacteria and fungi. This type of silver product has been used successfully in the management of acute and chronic wounds 3) Zinc sulfate is used on a limited basis. Studies recommend not mixing solutions containing Copper and Zinc with antibiotics due to the fact that tetracycline can be inactivated by these solutions.

4) Formaldehyde mixtures are used on a very limited bases as they lose their effectiveness quickly when exposed to air. It also has difficulty penetrating organic matter so living tissues must be cleaned prior to treatment. In spite of all that, the biggest drawback is formalin's toxicity. It is carcinogenic and poses a health hazard.

5) Acidified Sodium Chlorite, a broad spectrum antimicrobial, has been used in disinfecting and wound irrigation. However, because of its low pH (pH 2.3-3.2), it is corrosive to metal and equipment.

6) Iodine is used in the home, hospitals, emergency and trauma units. Claims as to its effectiveness as a wound wash application are well documented. However, iodine is easily inactivated by organic matter and it needs a long contact period with the living tissues to be effective. In wound management iodine is used in two forms:
   a. Cadexomer iodine—a polysaccharide starch lattice containing 0.9% elemental iodine that is released on exposure to wound exudate.
   b. PVP-1 (Povidone iodine)—an iodophor composed of elemental iodine and a synthetic polymer.

7) Hydrogen peroxide has been widely used for several years to clean, sanitize, irrigate and wash any open wounds. Care must be taken because the shelf-life of hydrogen peroxide is limited once it has been open. It is also degraded by light and UV rays. However, stabilized peroxide compounds are available that have a longer lasting antimicrobial effect.

8) For plants and trees, they must be pruned. When beginning a fungal treatment, remove any broken or dead branches from the tree. Do not remove any suckers until the fall. Treat any cut stub with fungicide. Clean your pruning tools with hot, soapy water or dipping them into fungicide and then rinsing them clean. This will keep the fungus from spreading to other trees. Remove any tree debris away from other healthy trees and burn it or dispose of it where other trees will not be harmed.

9) Treat the tree with fungicide. Apply the fungicides to the leaves and branches, and watered into the roots. Do not skip a treatment because it could allow the fungus to regrow.

SUMMARY OF THE INVENTION

The present disclosure relates to compositions and methods that are effective in controlling and preventing bacterial, viral and fungal infections in the living tissue of plants, humans and animals, and in advancing the healing process for wounds to that tissue. The disclosed compositions comprise a biocidal system, a pH buffer, and one or more of a surfactant, a cellular energy supplement, an inflammation reducer, a clotting agent, an electrolytic system and a lattice system and for plants a fungicide; all in an aqueous composition.

Additional advantages will be set forth in part in the description that follows and in part will be obvious from the description or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF THE EXEMPLARY EMBODIMENTS

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a carrier" includes mixtures of two or more such carriers, and the like.

"Optional" or "Optionally" as used herein means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations by use of the antecedent "about," it will be understood that the particular value forms another aspect. It will be further understood that the endpoints of each of the ranges are significant both in relation to the other endpoint and independently of the other endpoint.

A weight percent of a component, unless specifically stated to the contrary, is based on the total weight of the formulation or composition in which the component is included.

"Contacting" as used herein means an instance of applying a composition to the skin or wound.

"Sufficient Amount" and "Sufficient Time" as used herein means an amount and time needed to achieve the desired result or results, e.g., control and/or prevention of infection of the wound.

"Admixture" or "Blend" as used herein means a physical combination of two or more different components.

"Controlled Release" as used herein means the use of a material to regulate the release of another substance.

"Biocide" as used herein refers to compounds that are biologically active against a primary pathogen.

"Primary pathogen" as used herein refers to bacteria, viruses, fungi or other biologically active microorganisms that can cause infection in a wound.

"Dermal Environment" as used herein refers to the multiple layers of skin tissue associated with humans, animals or plants.

"Covalent bonds" as used herein means the forces that hold atoms together that share electrons and are referred to as strong bonds.

"Intermolecular Attractions" as used herein refers to the attractions between one molecule and a neighboring molecule.

"Microbiological" or "Microbial" as used herein refers to any inclusion or growth of harmful microorganisms such as mold, mildew, viral or bacterial contamination.

"Microbiological Count" as used herein refers to the amount or number of microbiological contaminates present on any surface or test sample.

"Pathogen" as used herein refers to mold, mildew, bacteria, viruses or other microorganisms that can cause contamination.

"1% solution" as used herein is defined as 1 part of an acid/salt mixture and 99 parts of water.

A "weight percent" of a component, unless specifically stated to the contrary, is based on the total weight of the formulation or composition in which the component is included.

"Cellular Energy supplement" as used herein refers to a product(s) that will supply energy to the damage cell or its neighboring cells to improve the healing process.

"Clotting agent" as used herein refers to reducing blood flow from a new or aggravated wound.

"Electrolytic System" as used herein refers to the electrolyte in a cell or nerve endings that would accommodate conduct and transmit an electrical impulse or current.

"Inflammation Reducer" as used herein refers to a product (s) that would reduce or inhibit the accumulation of any inflammation in a wound, bruise or injury.

"Surfactant" as used herein refers to compounds that lower the surface tension of a liquid, the interfacial tension between two liquids, or that between a liquid and a solid.

"Lattice forming system" as used herein refers to the bonding of the wound by using the lattice energy of the ionic nature of the cell and the electrolyte to seal the wound and improve the healing time.

"pH buffer" is used herein refers to a mixture that adjusts the pH level in a product.

The present disclosure addresses solutions to several unmet needs as defined below:
1. An antibiotic system that kills only desired pathogens and not good bacteria, yet has an effective kill rate of at least a 99.9%.
2. Energy source for accelerated cell repair
3. Inflammation reducer to prevent swelling, therefore faster healing
4. Anti-clotting agent to stop bleeding and blood lose
5. A lattice work for closing the wound and accelerating the healing process
6. The ability to flush and irrigate the wound in a single step
7. Providing compositions that are a replacement for biocides that contain heavy metals and are cacogenic
8. Providing compositions that aid in the creation of cell connective tissue neurons and nerve endings.

Treatment Compositions

A first disclosed composition that is effective in controlling and preventing bacterial, viral and fungal infections in the living tissue of plants, humans and animals, and in advancing the healing process for wounds to that tissue, which comprises of:
 a) from about 0.01% to about 15.0% by weight of a biocidal system comprising:
  i) from about 0.1% to about 5% by weight of a biocide; and
  ii) at least about 10% by weight of an pH buffer agent; and
 b) and one or more of c through j;
 c) from about 0.01% to about 10.0% by weight of fungicide agent
 d) from about 0.01% to about 5.0% by weight of cellular energy supplement e) from about 0.01% to about 3.0% by weight of an inflammation reducer
 f) from about 0.01% to about 3.0% by weight of clotting agent
 g) from about 0.01% to about 3.0% by weight electrolytes and minerals
 h) from about 0.01% to about 30.0% by weight lattice system
 i) from about 0.01% to 3.0% by weight of a surfactant; and
 j) from about 0.10% to about 4.0% by weight of a thickening agent; and
 k) the balance being an aqueous based carrier.

However, other non-limiting embodiments and combinations are possible as further disclosed herein.

Biocidal System

The disclosed compositions comprise a biocidal system. The biocidal system comprises a biocide and a pH buffer.

Biocide

Suitable biocides include quaternary ammonium compounds chosen from ($C_{12}$-$C_{14}$ alkyl)($C_1$-$C_2$ dialkyl)benzyl ammonium salts, N—($C_{12}$-$C_{18}$ alkyl)heteroaryl ammonium salts, and N—[($C_{12}$-$C_{14}$ alkyl)($C_1$-$C_2$ dialkyl)]heteroarylalkylene ammonium salts. Non-limiting examples of the ($C_{12}$-$C_{14}$ alkyl)($C_1$-$C_2$ dialkyl)benzyl ammonium salts include ($C_{12}$-$C_{14}$ alkyl)dimethyl-benzyl ammonium chloride, ($C_{12}$-$C_{14}$ alkyl)dimethylbenzyl ammonium bromide, and ($C_{12}$-$C_{14}$ alkyl)dimethylbenzyl ammonium hydrogen sulfate. Non-limiting examples of the N—($C_{12}$-$C_{18}$ alkyl)heteroaryl ammonium salts include cetyl pyridinium chloride, cetyl pyridinium bromide, and cetyl pyridinium hydrogen sulfide. For the N—($C_{12}$-$C_{18}$ alkyl)heteroaryl ammonium salts other anions can be used.

Further examples of quaternary ammonium compounds suitable for use as the primary biocides include cetyltrimethylammonium chloride, stearyltrimethylammonium chloride, isostearyltrimethylammonium chloride, lauryltrimethylammonium chloride, behenyltrimethyl-ammonium chloride, octadecyltrimethylammonium chloride, cocoyltrimethylammonium chloride, cetyltrimethylammonium bromide, stearyltrimethylammonium bromide, lauryl-trimethylammonium bromide, isostearyllauryldimethylammonium chloride, dicetyldimethyl-ammonium chloride, distearyldimethylammonium chloride, dicocoyldimethylammonium chloride, gluconamidopropyldimethylhydroxyethylammonium chloride, di[polyoxyethylene(2)]oleylmethylammonium chloride, dodecyldimethylethylammonium chloride, octyldihydroxyethylmethylammonium chloride, tri[polyoxyethylene(5)]-stearylammonium chloride, polyoxypropylenemethyldiethylammonium chloride, lauryl-dimethyl(ethylbenzyl)ammonium chloride, behenamidopropyl-N,N-dimethyl-N-(2,3-dihydroxypropyl)ammonium chloride, tallowdimethylammoniopropyltrimethylammonium dichloride, and benzalconium chloride.

Other biocides include copper, zinc, silver, salts of chlorides, chlorites, perchlorates, hypochlorites, sulfates, sulfites, bisulfates and bisulfites. Also colloid metal such as silver, gold, copper and zinc have superior biocidal properties. Colloidal silver, gold, copper and zinc are extracted and created as ultrafine (0.010-0.001 micron) particles. The beneficial natural elements of precious gold and silver, and primal elemental copper and zinc, can cure of illnesses, alleviation of pain. Other cures using colloidal metals as topical include their use in treating burns, and skin infections, other glandular problems, stress related pains and symptoms, also to clean the blood and circulatory system, boost collagen production and speed up synapse response of the brain.

Other suitable biocides include organic acids which are safe under the FDA GRAS guidelines for food production yet still effective in controlling bacteria.

The first group of suitable organic acids is Lactic, Acetic, Formic, Fumaric, Citric, Oxalic, Adipic and Uric.

The second group of suitable organic acids is the carboxylic acids, whose acidity is associated with their carboxyl group —COOH. Sulfonic acids, containing the group —$SO_2OH$, are relatively stronger acids. The relative stability of the conjugate base of the acid determines its acidity. In some biological systems more complex organic acids such as L-lactic, citric, and D-glucuronic acids are formed. These use the hydroxyl or carboxyl group.

The third group of suitable organic acids is Humic, Sebacic, Stearic, Gallic, Palmitic, Caffeic, Glyoxylic, Fulvic, Carnosic, Anthranilic, Ellagic, Lipoic, Chlorogenic, Rosmarinic, Phosphoric, Methacrylic, Oleanic, Nitrohumic, Florocinnamic, Hexaflorosilicic, Hydrofluoric, Hydroxycitric and Silicofluoric.

The fourth group of suitable organic acids is fruit acids. The acids in fruits are chiefly acetic, malic, citric, tartaric, oxalic, and in some instances boric. Malic acid is present in apples, pears, currants, blackberries, raspberries, quince, pineapple, cherries, and rhubarb. Citric acid is found in lemons, oranges, grapefruit, lemons, limes, quince, gooseberry, strawberry, raspberry, currant, and cranberry. Tartaric acid occurs in grapes. Boric acid is found in many fresh fruits and vegetables. Mandelic acid is present in almonds.

The fifth group of suitable organic acids is beta hydroxy acids, which is a type of phenolic acid. Salicylic acid is a colorless crystalline organic acid whose main active ingredient obtained from this source is a monohydroxiybenzoic acid.

The sixth group of suitable organic acids is a class of products that break biofilm. Biofilms are the protective layer/barrier that surround bacteria. Some species are not able to attach to a surface on their own but are often able to anchor themselves to the matrix or the bacteria cells. It is during this colonization that the cells are able to communicate via its quorum sensing ability. Once colonization has begun, the biofilm grows through a combination of cell division and recruitment. The final stage of biofilm formation is known as development and is the stage in which the biofilm is established and may only change in shape and size. The development of a biofilm may allow for an aggregate cell colony to be increasingly resistant. A biofilm's hard protective surface can be broken by *Lactobacillus* sc *Nisin* which is produced by fermentation using the bacterium *Lactococcus lactis*. This is obtained from the culturing of *Lactococcus lactis* on natural substrates, such as milk or dextrose, and is not chemically synthesized. This is a peptide which is produced by the food grade dairy starter bacterium *Lactococcus lactis*.

A seventh group of suitable organic acids is natural enzymes. Enzymes are proteins that catalyze chemical reactions and range from just 62 amino acid residues. Typically these are protease, lipase, diastase and cellulase enzymes. Enzymes are usually very specific as to which reactions they catalyze and the substrates that are involved in these reactions. The shape, charge and hydrophilic/hydrophobic nature characterize the enzymes.

pH Buffer

A dermal, non-corrosive acid composition, having a maximum proton count of $1.5 \times 10^{25}$, an embodied conductivity range of from 250 mV to 1500 mV and a 0.1% solution of the composition having a pH of under 2.0.

Cellular Energy Supplement

A cellular energy supplement is product that will supply energy to the damage cell or its neighboring cells to improve the healing process. Such products suitable to energize the cell are vitamins and amino acids.

The suitable vitamins are niacin which can be either of its two structures which is nicotinic acid and nicotinamide. This is also called vitamin B3. There are two co-enzyme forms of niacin: nicotinamide adenine dinucleotide (NAD) and nicotinamide adenine dinucleotide phosphate (NADP). Both play an important role in energy transfer reactions in the metabolism of glucose, fat and alcohol. NAD carries hydrogens and their electrons during metabolic reactions, including the pathway from the citric acid cycle to the electron transport chain. NADP is a coenzyme in lipid and nucleic acid synthesis.

Vitamin is B5 chemically known as Pantothenic Acid which is involved in the oxidation of fatty acids and carbohydrates. Coenzyme A, which can be synthesized from panothenic acid, is involved in the synthesis of amino acids, fatty acids, ketones, cholesterol, phospholipids, steroid hormones, neurotransmitters and antibodies.

Vitamin B7 also known as Biotin which plays a key role in the metabolism of lipids, proteins and carbohydrates. It is a critical co-enzyme of four carboxylases: acetyl CoA carboxylase, which is involved in the synthesis of fatty acids from acetate; propionyl CoA carboxylase, involved in gluconeogenesis; β-methylcrotonyl CoA carboxylase, involved in the metabolism of leucin; and pyruvate CoA carboxylase, which is involved in the metabolism of energy, amino acids and cholesterol Vitamin B12 is involved in the cellular metabolism of carbohydrates, proteins and lipids. It is essential in the production of blood cells in bone marrow, nerve sheaths and proteins. Vitamin B12 functions as a co-enzyme in intermediary metabolism for the methionine synthase reaction with methylcobalamin, and the methylmalonyl CoA mutase reaction with adenosylcobalamin.

Amino acids are the chemical that make up proteins, and are called the "building blocks" of protein Amino acids combine with nitrogen and form thousands of different proteins. There are twenty-eight commonly known amino acids of which 9 are called essential amino acids. The remaining 19 are non-essential amino acids, meaning they can be manufactured by the body from other amino acids as needed, but they too can be obtained through supplements.

L-arginine is a non-essential amino acid is involved in a number of different functions in the body. They include wound healing, helping the kidneys remove waste products from the body and maintaining immune and hormone function. In the body, the amino acid arginine changes into nitric oxide (NO). Nitric oxide is a powerful neurotransmitter that helps blood vessels relax and also improves circulation. Some evidence shows that arginine may help improve blood flow in the arteries of the heart. That may improve symptoms of clogged arteries, chest pain or angina, and coronary artery disease.

Inflammation Reducer

Inflammation is part of the complex biological response of vascular tissues to harmful stimuli, such as pathogens, damaged cells, or irritants. These signs of acute inflammation are pain, heat, redness swelling, and loss of function. Inflammation is a protective attempt by the organism to remove the injurious stimuli and to initiate the healing process. Inflammation can be caused by in impact injury, a repetitive strain injury, an accident at work, a pulled muscle.

Some inflammation reducers are essential oils such as thyme, clove and fennel; rose; *eucalyptus*; and even the citrus bergamot. The oils considered to have the strongest anti-inflammation. Traditional medicine has long used herbal preparations to reduce inflammation of wounds or achy muscles and joints. Massage therapists have long known that certain essential oils can help speed the healing of their clients, and home users have found the same result with arthritic and rheumatic conditions.

Anti-inflammatory medications are commonly taken to treat conditions caused by inflammation such as arthritis, ankylosing spondylitis, tendonitis, bursitis, gout, fever or menstrual cramps. These medications reduce chemical signals that cause pain and inflammation in the body, specifically at the injured area. There are 3 different kinds of OTC (over the counter):
1. NSAIDs (nonsteroidal anti-inflammatory drugs). These include aspirin, ibuprofen (Advil and Motrin), naproxen sodium (Aleve), and ketoprofen (Orudis KT).
2. Acetaminophen such as Tylenol and Panadol.
3. Aspirin is also considered one of the best OTC medications that a patient can take for pain relief. Aspirin is particularly effective in treating migraine headaches. Although effective for migraines, aspirin can also be used to treat other inflammatory conditions that may cause pain. Of note, aspirin inhibits platelets, which can result in long-term blood-thinning. Thus, a patient with a cut, bruise or other injury from trauma should seek emergency medical treatment to make sure that bleeding is adequately controlled.

Clotting Agent

An antihemorrhagic agent is a substance that promotes hemostasis or stops bleeding. It may also be known as a hemostatic agent. The different types of antihemorrhagic agents used in medicine have various mechanisms of action:
1. Systemic drugs work by inhibiting fibrinolysis or promoting coagulation.
2. Locally-acting hemostatic agents work by causing vasoconstriction or promoting platelet aggrega.
3. Styptics are a specific type of antihemorrhagic agent that works by contracting tissue to seal injured blood vessels. Styptic pencils contain astringents.
4. Microfibrillar collagen hemostat is a topical agent composed of re-sorbable microfibrillar collagen. It attracts platelets and allows for the formation of a blood clot when it comes into contact with blood.
5. Chitosan hemostats are topical agents composed of chitosan and its salts. Chitosan bonds with platelets and red blood cells to form a gel-like clot which seals a bleeding vessel. Unlike other hemostat technologies its action does not require the normal hemostatic pathway and therefore continues to function even when anticoagulants like heparin are present.
6. Other ingredients such as anhydrous aluminium sulfate, potassium alum or titanium dioxide which is applied directly to the bleeding site. The high ionic strength promotes flocculation of the blood, and the astringent chemical causes local vasoconstriction.
7. Styptic powder is used in the veterinary trade to stop bleeding from nails that are clipped too closely. This powder is used on animals, such as dogs, cats, rabbits, and birds, where the vein is found in the center of the nail.

Electrolytic System

An electrolyte is normally described as a liquid or gel that contains ions and can be decomposed by electrolysis as with a battery. Commonly, electrolytes are solutions of acids, bases, or salts. Furthermore, some gases may act as electrolytes under conditions of high temperature or low pressure. Electrolyte solutions can also result from the dissolution of some biological polymer like DNA and polypeptides, and synthetic polymers like polystyrene sulfonate and polyelectrolytes, which contain charged functional groups.

Blood tests check electrolytes, the minerals that help keep the body's fluid levels in balance, and are necessary to help the muscles, heart, and other organs work properly. Blood tests for electrolytes measure levels of sodium, potassium, chloride, and bicarbonate in the body.
1. Sodium plays a major role in regulating the amount of water in the body. Also, the passage of sodium in and out of cells is necessary for transmitting electrical signals in the brain and in the muscles.
2. Potassium is essential to regulate how the heart beats.
3. Chloride, like sodium, helps maintain a balance of fluids in the body. If there's a large loss of chloride, the blood may become more acidic and prevent essential chemical reactions from occurring.
4. Bicarbonate prevents the body's tissues from getting too much or too little acid.

5. Blood urea nitrogen (BUN) is a measure waste product that's created when the body breaks down protein. Dehydration, excessive bleeding, and severe infection leading to shock can also elevate the BUN levels in the blood.
6. Creatinine levels in the blood that are too high can indicate that the kidneys aren't working properly. The kidneys filter and excrete creatinine. Dehydration and muscle damage also can raise creatinine levels.

Surfactant

A surfactant component includes ingredients that modify the water in the system making it suitable from use with several types of water such as hard water, soft water, sulfite contaminated water, rain water, pond water, well water or calcium rich water. Quaternary ammonium compounds which are more compatible with anionic surfactants generally have an inadequate conditioning effect.

In-order to improve the performance of an aqueous mixture dialkyl diallyl ammonium chloride/acrylic acid-type polymers is added. This method for improving the stickiness properties of the composition encompasses adding an effective amount of a polymer comprising:
  I. about 60 to about 99%, based on total polymer weight, of a quaternary diallyl dialkyl ammonium monomer, wherein alkyl groups are independently selected from alkyl groups of 1 to 18 carbon atoms, preferably $C_1$-4 alkyl, and wherein said quaternary diallyl dialkyl ammonium monomer's counterion is selected from the group consisting of conjugate bases of acids having an ionization constant greater than $10^{-13}$, more preferably selected from the group consisting of fluoride, chloride, bromide, hydroxide, nitrate, acetate, hydrogen sulfate, and primary phosphates; and
  II. about 1 to about 40%, based on total polymer weight, of an anionic monomer selected from the group consisting of acrylic acid and methacrylic acid; wherein the average molecular weight of said polymer ranges from about 50,000 to about 10,000,000, as determined by gel permeation chromatography.

The polymer base can also be a combination of one or more bases, for example, glycerol in combination with ethoxylated partial glyceride fatty acid esters. These include branched chain esters, ethoxylated partial glyceride fatty acid esters, protein derivatives, lanolin and lanolin derivatives, and fatty alcohol ethoxylates, emollient oils, fatty acids, fatty alcohols and their esters. Other examples of suitable bases include glycerine, sortibal aloe, poylglycols, polyethylene glycol, polyoxyethylene and polyethylene oxide.

Lattice Forming

The open wound would heal faster from the use of lattice energy of an ionic nature of the cell and the body's electrolytic fluids to strength of bonds in that ionic compound. The lattice energy is accelerated by the use of carbohydrates, monosaccharaides, disaccharides and polysaccharides. These are glucose, dextrose, fructose, galactose, sucrose, maltose, lactose, deoxyribose, and ribose.

Fungicide

For plants, fungicides can either be contact, trans laminar or systemic. Contact fungicides are not taken up into the plant tissue, and only protect the plant where the spray is deposited; trans laminar fungicides redistribute the fungicide from the upper, sprayed leaf surface to the lower, unsprayed surface; systemic fungicides are taken up & redistributed through the xylem vessels to the upper parts of the plant.

Some natural fungicides are:
Tea tree oil, Cinnamaldehyde, Cinnamon essential oil, Jojoba oil, Neem oil, Rosemary oil, Monocerin, *Ampelomyces quisqualis*.

A full list of other fungicides are:
(3-ethoxypropyl) mercury bromide, 2-methoxyethylmercury chloride, 2-phenylphenol, 8-hydroxyquinoline sulfate, 8-phenylmercurioxyquinoline, acibenzolar. acylamino acid fungicides, acypetacs, aldimorph, aliphatic nitrogen fungicides, allyl alcohol, amide fungicides, ampropylfos, Anilazine, anilide fungicides, antibiotic fungicides, aromatic fungicides, aureofungin, azaconazole, azithiram, azoxystrobin, barium polysulfide, benalaxyl, benalaxyl-M, benodanil, benomyl, benquinox, bentaluron, benthiavalicarb benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, bixafen, blasticidin-S, Bordeaux mixture, boric acid, boscalid, bridged diphenyl fungicides, bromuconazole, bupirimate, Burgundy mixture, buthiobate, sec-butylamine, calcium polysulfide, captafol, captan, carbamate fungicides, carbamorph, carbanilate, fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper(II) sulfate, copper sulfate, basic copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, diniconazole-M, dinitrophenol fungicides, dinobuton, dinocap, dinocap-4, dinocap-6, dinocton, dinopenton, dinosulfon, dinoterbon, diphenylamine, dipyrithione, disulfiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, Fluconazole, fludioxonil, flumetover, flumorph, fluopicolide, fluoroimide, fluotrimazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine inorganic fungicides, inorganic mercury fungicides, iodomethane, ipconazole, iprobenfos, iprodione, iprovalicarb, isoprothiolane, isovaledione, kasugamycin, kresoxim-methyl, Lime sulfur (lime sulphur), mancopper, mancozeb, maneb, mebenil, mecarbinzid, mepanipyrim, mepronil, mercuric chloride, mercuric oxide, mercurous chloride, mercury fungicides, metalaxyl, metalaxyl-M (a.k.a. Mefenoxam), metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulfonanilide, nabam, natamycin, nystatin, nitrostyrene, nitrothal-isopropyl, nuarimol, OCH, octhilinone, ofurace, oprodione, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate, fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinomethionate, quinone fungicides, quinoxaline fungicides, quinoxyfen, quintozene, rabenzazole, salicylanilide, silthiofam, silver, simeconazole, sodium azide, sodium bicarbonate, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, triforine, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, Undecylenic acid, uniconazole, uniconazole-P, urea fungicides, validamycin, valinamide fungicides, vinclozolin, voriconazole, zarilamid, zinc naphthenate, zineb, ziram, zoxamide

Aqueous Carrier

The balance of the disclosed compositions comprises a carrier. The carrier can be any suitable material that can dissolve the active ingredients and co-ingredients and deliver the biocidal system to the infected areas or the wound. Water is a convenient carrier for liquid embodiments of the disclosed composition.

Formulations

The following are non-limiting examples of the disclosed compositions:

TABLE 1

| Ingredients | 1 | 2 | 3 | 4 | 5 |
|---|---|---|---|---|---|
| cetyl pyridinium chloride | 0.10 | 0.25 | 0.35 | 0.50 | 0.25 |
| pH buffer | 2.0 | 2.0 | 2.0 | 2.0 | 2.0 |
| PEG 6 | 1.0 | 1.0 | 1.0 | 1.0 | 1.0 |
| surfactant | 2.0 | 3.0 | 3.0 | 3.0 | 3.0 |
| xanthan gum | 0.5 | 0.5 | 0.5 | 0.5 | 1.0 |
| cellular energy supplement- B3, 5, 6, 7, 12 & L-Arginine | 0.3 | 0.3 | 0.3 | 0.3 | 0.3 |
| inflammation reducer- clove oil | 0.5 | 0.5 | 0.5 | 1.0 | 1.0 |
| clotting agent- anhydrous aluminum sulfate | 0.25 | 1.0 | 0.5 | 0.5 | 1.0 |
| Lattice forming system- sucrose | 10.0 | 10.0 | 10.0 | 20.0 | 20.0 |
| carrier | balance | balance | balance | balance | balance |

Methods of Use

The disclosed compositions can be used for various applications with the application methods and dosage regimens dictated by the frequency of contamination and infection.

1) Spray applications usually consist of a composition that is enough to cover any open wound, or living tissue. The biocidal composition must cover enough so as to make contact with any infected area of the wound.
2) Foam applications are effective where the foam composition can be applied directly to the open wound in order to insure it is thoroughly coated with the foam.
3) Gel applications can be utilized where the gel's thickness which will allow the embodied composition to penetrate a wound, help stop the bleeding, seal the wound from contaminants, block air borne infection, accelerate the healing process and help mend the wound and where a longer contact period is beneficial.
4) A wrap application can be used to apply the embodied composition in manner a that will allow the infected area to be kept free of moisture, thereby allowing the biocidal composition the longest contact period with the infected tissue.

Test Results

The following procedures can be used to evaluate the disclosed compositions against various microorganisms:

Bacterial testing was completed at BSK Food Laboratory located in Fresno Calif. using *E. coli* ATCC #25922 strain. The exposure time was 60 seconds and the results are listed in Table A. The reduction in bacterial growth was 99.999%.

TABLE 2

| Sample | Control units | Results units |
|---|---|---|
| Biocide 0.15% | 999,000 cfu/ml | <1 cfu/ml |
| Biocide 0.30% | 999,000 cfu/ml | <1 cfu/ml |
| Biocide 0.5% | 999,000 cfu/ml | <1 cfu/ml |

*cfu—colony forming units

Bacterial testing was done using *Staphylococcus aureus* ATCC #6538. The results are listed in Table B. The reduction in bacterial growth was a 99.9999%.

TABLE 3

| Species | Control units | Results units |
|---|---|---|
| Staphylococcus aureus | 7.9 × 10^7 cfu/ml | 2.5 cfu/ml |

Bacterial testing was completed at Biological Consulting Services of North Florida, Inc on *E. coli* (ATCC 15597), *Salmonella enterica* (ATCC BAA-711), and Methicillin Resistant *Staphylococcus aureus* (MRSA; BAA-44). The results are listed in Table C.

TABLE 4

| Sample | Control units (cfu/ml) | Results units (cfu/ml) |
|---|---|---|
| E. coli | 9.3 × 10^5 | <0.5 |
| S. enterica | 1.1 × 10^6 | <0.5 |
| MRSA | 1.0 × 10^6 | <0.5 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A composition that is effective in controlling bacterial, viral and fungal infections in living tissue of humans and animals and in advancing a healing process for wounds to the living tissue, the composition comprising:
    a) from about 0.01% to about 15.0% by weight of a biocidal system comprising from about 0.01% to about 5.0% by weight of a biocide and at least about 10% by weight of a pH buffer agent; and
    b) from about 0.01% to about 5.0% by weight of a cellular energy supplement selected from the group consisting of nicotinamide, nicotinamide adenine dinucleotide, and nicotinamide adenine dinucleotide phosphate;
    c) one or more of d) through i), wherein d) through i) comprise:
    d) from about 0.01% to about 3.0% by weight of an inflammation reducer;
    e) from about 0.01% to about 3.0% by weight of a clotting agent;
    f) from about 0.01% to about 3.0% by weight electrolytes and minerals;
    g) from about 0.01% to about 30.0% by weight of a lattice forming system;
    h) from about 0.01% to 3.0% by weight of a surfactant; and
    i) from about 0.10% to about 4.0% by weight of a thickening agent; and
    j) wherein a balance of the composition comprises an aqueous based carrier.

2. The composition according to claim 1, wherein the biocide is a quaternary ammonium salt comprising at least one aryl or heteroaryl unit.

3. The composition according to claim 2, wherein the biocide is cetyl pyridinium chloride.

4. The composition according to claim 1, wherein the pH buffer agent is a dermal, non-corrosive acid composition, having a maximum proton count of $1.5 \times 10^{25}$, an embodied conductivity range of from 250 mV to 1500 mV and a 0.1% solution of the composition having a pH of under 2.0.

5. The composition according to claim 1, wherein the inflammation reducer is chosen from thyme, clove, eucalyptus, NSAIDs Acetaminophen, and aspirin.

6. The composition according to claim 1, wherein the inflammation reducer is an essential oil or clove oil.

7. The composition according to claim 1, wherein the clotting agent is a Systemic drug comprising one or more of, a locally-acting hemostatic agent, a topical Microfibrillar collage to attract platelets to form blood clot, a topical Chitosan hemostat salt, anhydrous aluminium sulfate, potassium alum, or titanium dioxide.

8. The composition according to claim 1, wherein the clotting agent is anhydrous aluminium sulfate.

9. The composition according to claim 1, wherein the composition further comprises an electrolytic system chosen from salts of sodium, potassium, Chloride, Bicarbonate, Blood urea nitrogen (BUN) and Creatinine.

10. The composition according to claim 9, wherein the electrolytic system is blend of sodium and potassium chloride.

11. The composition according to claim 1, wherein the lattice forming system is chosen from carbohydrates monosaccharaides, disaccharides polysaccharides selected from the group consisting of: glucose, dextrose, fructose, galactose, sucrose, maltose, lactose, deoxyribose, and ribose.

12. The composition according to claim 1, wherein the lattice forming system is sucrose.

13. The composition according to claim 1, wherein the thickening agent is chosen from hydroxynethyl cellulose, hydroxyethyl cellulose, methylcellulose, hydroxypropyl cellulose, methyl cellulose, carboxy methylcellulose, emulsifying waxes, alkyl triammonium methosulfate, and ceteraryl octanoate.

14. The composition according to claim 1, wherein the thickening agent is hydroxyethyl cellulose.

15. The composition according to claim 1, wherein the thickening agent is chosen from polysaccharides and linear sulfated polysaccharides.

16. The composition according to claim 1, wherein the thickening agent is a poylsaccharides starch which can be unmodified or modified using acid, enzymes, alkaline, bleached, oxidized, acetylated, hydroxpropylated, octenylsuccinic anhydride, carboxyethylated, phosphate, hydroxypropyl, acetylated oxidated, cationic, cold water, pregelatinized and instant starch.

17. The composition according to claim 1, wherein the inflammation reducer is selected from the group consisting of fennel, rose, and citrus bergamot.

18. The composition according to claim 1, wherein the composition further includes a fungicide comprising one or more of tea tree oil, cinnamaldehyde, cinnamon essential oil, jojoba oil, neem oil, rosemary oil, monocerin, and ampelomyces quisqualis.

\* \* \* \* \*